United States Patent
Cai et al.

(10) Patent No.: US 6,998,478 B1
(45) Date of Patent: Feb. 14, 2006

(54) ISOLATION AND CHARACTERIZATION OF A FIBER-SPECIFIC β-TUBULIN PROMOTER FROM COTTON

(75) Inventors: Lin Cai, Singapore (SG); Xuebao Li, Singapore (SG); Ninghui Cheng, Houston, TX (US); Jian-Wei Liu, Singapore (SG)

(73) Assignee: Temasek Life Sciences Laboratory Limited, Singapore (SG)

( * ) Notice: Subject to any disclaimer, the term of this patent is extended or adjusted under 35 U.S.C. 154(b) by 580 days.

(21) Appl. No.: 10/089,543

(22) PCT Filed: Aug. 1, 2000

(86) PCT No.: PCT/SG00/00111

§ 371 (c)(1),
(2), (4) Date: Aug. 4, 2002

(87) PCT Pub. No.: WO02/10377

PCT Pub. Date: Feb. 7, 2002

(51) Int. Cl.
*C07H 21/04* (2006.01)
(52) U.S. Cl. .................... 536/24.1; 536/23.1
(58) Field of Classification Search .............. 536/23.1, 536/24.1; 435/320.1, 410, 468, 419, 427, 435/69.1
See application file for complete search history.

(56) References Cited

U.S. PATENT DOCUMENTS 5,792,933 A    8/1998  Ma

FOREIGN PATENT DOCUMENTS

WO    WO 96/39021    12/1996

OTHER PUBLICATIONS

Maliyakal, E.J. et al. (1992). "Gene expression in cotton (*Gossypium hirsutum* L.) fiber: Cloning of the mRNAs," *Proc. Natl. Acad. Sci USA* 89:5769-5773.
Koga-Ban, Y. et al. (1995). "cDNA Sequences of Three Kinds of β-tubulins from Rice," *DNA Research* 2:21-26.
Rinehart, J.A. et al. (1996). "Tissue-Specific and Developmental Regulation of Cotton Gene FbL2A," *Plant Physiol.* 112:1331-1341.
Dang, P.M. et al. (1996). "Expression of a 'cotton fiber specific' gene, Gh-1, in transgenic tobacco and cotton," *Plant Physiology*, vol. III:55, No. 135.

*Primary Examiner*—Terry McKelvey
*Assistant Examiner*—Jennifer Dunston
(74) *Attorney, Agent, or Firm*—Rothwell Figg Ernst & Manbeck

(57) ABSTRACT

The present invention relates to a cotton β-tubulin gene CFTUB2, and active fragments thereof. These promoters show strong fiber-specific activity.

2 Claims, 3 Drawing Sheets

```
GGCACGAGTATATTTTTCCTCTCCAATTTTCCGTCACTTTCCCGAGAAAATGAGAGAAATC
CTTCACATCCAAGGTGGCCAATGCGGCAATCAGATAGGAGCCAAGTTCTGGGAAGTCGTA
TGTGCCGAACATGGCATCGATTCAACGGGTCGATATGGTGGTGACTCGGAGCTCCAGCTT
GAGCGAATCAATGTTTACTACAACGAAGCCAGTTGTGGCCGTTTTGTTCCCCGCGCAGTTT
TAATGGATCTGGAACCCGGAACCATGGATAGCGTAAGATCCGGTCCTTACGGACAAATTT
TCCGACCCGATAACTTCGTTTTCGGACAGTCCGGTGCGGGAAACAATTGGGCTAAGGGAC
ATTACACTGAAGGAGCGGAGCTTATCGATTCCGTTCTCGACGTGGTTAGAAAGGAAGCCG
AAAATTGCGATTGCTTGCAAGGGTTTCAGGTATGCCATTCTTTGGGAAGAAGAACGGGTT
CCGGAATGGGAACGTTGTTGATATCGAAGATACGAGAGGAGTATCCGGACCGAATGATGC
TTACGTTTTCGGTGTTTCCATCTCCCAAGGTTTCTGATACTGTTGTTGAACCTTACAACGCG
ACACTCTCAGTTCATCAGCTTGTGGAAAATGCTGATGAGTGTATGGTTCTTGATAACGAAG
CTCTCTACGATATCTGTTTCCGTACCCTCAAGCTCACTACTCCAAGTTTTGGAGATCTCAAC
CATCTAATTTCTGCCACCATGAGTGGTGTAACATGCTGCCTTCGCTTCCCTGGTCAGCTTA
ACTCAGATCTCCGCAAACTTGCTGTAAACCTTATTCCATTCCCTCGACTACATTTCTTCATG
GTGGGATTTGCGCCTCTCACCTCACGCGGTTCCCAACAGTACAGAGCCCTCACTGTCCCTG
AACTTACACAGCAAATGTGGGATGCCAAGAACATGATGTGTGCAGCTGATCCTCGACACG
GTCGATACCTCACAGCATCAGCGGTCTTCCGTGGGAAGATGAGCACGAAAGAGGTTGATG
AGCAGATGATCAATGTGCAAAACAAGAACTCATCTTACTTTGTTGAATGGATCCCGAACA
ATGTGAAGTCCACTGTTTGTGACATCCCTCCAATCGGCTTAAAGATGGCATCCACATTTAT
CGGGAACTCTACTTCAATCCAAGAGATGTTCAGGAGGGTGAGTGAACAATTCACTGCCAT
GTTCCGTAGGAAAGCTTTCTTGCATTGGTATACTGGAGAAGGGATGGATGAGATGGAGTT
CACAGAAGCGGAGAGTAACATGAATGACTTGGTTTCTGAGTACCAACAATACCAGGATGC
AACTGCAGATGATGAAGAGTACGAGGAAGAGGAGGAATACGAGGCAGAGGCTTAAAATC
TAATGGAATAATTTGGATGTTTTTCGTTGTGTTTTGGATTGGGCTTGTGGAGTGTGTTGATG
CAATTTCTCACTGCCTGTTTTTGGTCTTTGGATCACTGTATTGTTGATTGTGTCGACTTTAG
TTTTGTCCTCACAGCTTACGGAGTATATGTTGTTGTATTGCTTGTTGATTCATCTTATAAGT
AATTTCTAGTACACCTTAAGTAAAAAAAAAAAAAAAAAAAAAAAAAA
```

Fig. 1

```
ACTATAGGGCACGCGTGGTCGACGGCCCGGGCTGGTGCTTGATATCTATGATTTTCAGATT
TGCATAAGACTTCTATCTATCAGAAGACGCCTGCAGAGGATCCCAAATTAGTCTAAAATT
ATCTTCAGTCTCGGAAACCAACTCAGGACCCAAAACCCGTCGCTCACCCAACTCAGTCTA
ATATAACAGAGTATGACACTTATGACCATATAGAGCCTCGTAAGGTGCCATCTAGATGCC
AGATTGGAAACTGTTATTGTAGGCGAACTCAACTAACGGTAAAAAATCCTCTCAACTACC
TTAGTAATAAATCACATAGCTCCAAATCGTATCCTCTAGTATATGAATCACCTTCTCAAAT
TGACCATCGGTCTGAGGATGGAATGCAGACCGGTGCCACCGATTTACTAATGGTACCTAT
AAAAAATTATTATTTTTTAAAAAATTGATGTGACCAGTGGTTGGAGAGAGAGGTCTACCG
ATTGGTCAAGTGGCACCAATTTTTTATTTTACCTCCTGCCTAGATTCGTAAATACTATTGCA
TTTATCTCATTTCATTATTTATTTAATTATTTTATATTATTTGGATAAAAATTCTAATACTTT
ACTTTTTTTTAAAAAGAATTTATTTAATTATTTTATATTATTTAGATAAAAATTCTAATACT
TTACTTTTTTTTTAAAAAGAATTTCAATTGCGTTTTTTCTTAATTTAGTTTTAATTCTATACT
AATTATAAAAATTCTGATCGGATTAGTGTGGTGTCAAAGTCAAGTCACATGAATTTTGTTG
GAGAAAAAATAAAAATTAAACACATTTTTCGATTAATTTATTATATATATAATAATATAAA
CACATTTTTATTTAATGTTGTCAATAATATTTTTTAATTAAAATTTCAGCACAACAATTACA
CTCTCATCATTAAATTTAATCTTATTACCATAATTAAAATTGTGAGGACAATTATTTTTTAA
TCTCACCCTCCATTAATGCATATTATTAATTTTTGTTCGATACTTCTTATTTCACTCCTAACA
TTAATCATTAACCCAATTTTGAACTGTTATAATTTCTTAACTTATTCACTATTGTGGCTCTG
GGTCCATCTGGAAAGGCCACCGTCCAGGCTGTCCAACCACACTTTGCCACGTCATCAATTC
CAGTAACTACATTGTTACAGTTACTAAGCAAATCCCAATTTCAAAAATTCAATTTCCCAGG
AAAACGAAACGTCCGTTACTAACCGACCTAAAACCCAGCTCAACCTGCCGTCAATTAACG
GAAATCTTTTAACTCCTCTATATAACCCAAAACCACTCTCATCACCATTTCCCCATAAAAA
GAATTTCCGGAATTCTTATTCCTTTTATATTTTTCCTCTCCAATTTCCCGTCACTTTCCGGAG
AAAATGAGAGAAATCCTTCACATC
```

Fig. 2

CFTUB2 gene
pBITUB vectors
Fig. 3

SEQUENCE LISTING

<160> NUMBER OF SEQ ID NOS: 2

<210> SEQ ID NO 1
<211> LENGTH: 1623
<212> TYPE: DNA
<213> ORGANISM: Arabidopsis sp.

<400> SEQUENCE: 1

| | | | | | |
|---|---|---|---|---|---|
| ggcacgagta | tattttcct | ctccaatttt | ccgtcactt | cccgagaaaa | tgagagaaat | 60 |
| ccttcacatc | caaggtggcc | aatgcggcaa | tcagatagga | gccaagttct | gggaagtcgt | 120 |
| atgtgccgaa | catggcatcg | attcaacggg | tcgatatggt | ggtgactcgg | agctccagct | 180 |
| tgagcgaata | aatgtttact | acaacgaagc | cagttgtggc | cgttttgttc | cccgcgcagt | 240 |
| tttaatggat | ctggaacccg | gaaccatgga | tagcgtaaga | tccggtcctt | acggacaaat | 300 |
| tttccgaccc | gataacttcg | ttttcggaca | gtccggtgcg | ggaaacaatt | gggctaaggg | 360 |
| acattacact | gaaggagcgg | agcttatcga | ttccgttctc | gacgtggtta | aaaggaagc | 420 |
| cgaaaattgc | gattgcttgc | aagggtttca | ggtatgccat | tctttgggaa | gaagaacggg | 480 |
| ttccggaatg | ggaacgttgt | tgatatcgaa | gatacgagag | gagtatccgg | accgaatgat | 540 |
| gcttacgttt | tcggtgtttc | catctcccaa | ggtttctgat | actgttgttg | aaccttacaa | 600 |
| cgcgacactc | tcagttcatc | agcttgtgga | aaatgctgat | gagtgtatgg | ttcttgataa | 660 |
| cgaagctctc | tacgatatct | gtttccgtac | cctcaagctc | actactccaa | gttttggaga | 720 |
| tctcaaccat | ctaatttctg | ccaccatgag | tggtgtaaca | tgctgccttc | gcttccctgg | 780 |
| tcagcttaac | tcagatctcc | gcaaacttgc | tgtaaacctt | attccattcc | ctcgactaca | 840 |
| tttcttcatg | gtgggatttg | cgcctctcac | ctcacgcggt | tcccaacagt | acagagccct | 900 |
| cactgtccct | gaacttacac | agcaaatgtg | ggatgccaag | aacatgatgt | gtgcagctga | 960 |
| tcctcgacac | ggtcgatacc | tcacagcatc | agcggtcttc | cgtgggaaga | tgagcacgaa | 1020 |
| agaggttgat | gagcagatga | tcaatgtgca | aacaagaac | tcatcttact | tgttgaatg | 1080 |
| gatcccgaac | aatgtgaagt | ccactgtttg | tgacatccct | ccaatcggct | aaagatggc | 1140 |
| atccacattt | atcgggaact | ctacttcaat | ccaagagatg | ttcaggaggg | tgagtgaaca | 1200 |
| attcactgcc | atgttccgta | ggaaagcttt | cttgcattgg | tatactggag | aagggatgga | 1260 |
| tgagatggag | ttcacagaag | cggagagtaa | catgaatgac | ttggtttctg | agtaccaaca | 1320 |
| ataccaggat | gcaactgcag | atgatgaaga | gtacgaggaa | gaggaggaat | acgaggcaga | 1380 |
| ggcttaaaat | ctaatggaat | aatttggatg | tttttcgttg | tgttttggat | tgggcttgtg | 1440 |
| gagtgtgttg | atgcaattc | tcactgcctg | tttttggtct | ttggatcact | gtattgttga | 1500 |
| ttgtgtcgac | tttagttttg | tcctcacagc | ttacggagta | tatgttgttg | tattgcttgt | 1560 |
| tgattcatct | tataagtaat | ttctagtaca | ccttaagtaa | aaaaaaaaa | aaaaaaaaa | 1620 |
| aaa | | | | | | 1623 |

<210> SEQ ID NO 2
<211> LENGTH: 1433
<212> TYPE: DNA
<213> ORGANISM: Arabidopsis sp.

<400> SEQUENCE: 2

| | | | | | |
|---|---|---|---|---|---|
| actatagggc | acgcgtggtc | gacggcccgg | gctggtgctt | gatatctatg | attttcagat | 60 |
| ttgcataaga | cttctatcta | tcagaagacg | cctgcagagg | atcccaaatt | agtctaaaat | 120 |

-continued

```
tatcttcagt ctcggaaacc aactcaggac ccaaaacccg tcgctcaccc aactcagtct      180
aatataacag agtatgacac ttatgaccat atagagcctc gtaaggtgcc atctagatgc      240
cagattggaa actgttattg taggcgaact caactaacgg taaaaaatcc tctcaactac      300
cttagtaata aatcacatag ctccaaatcg tatcctctag tatatgaatc accttctcaa      360
attgaccatc ggtctgagga tggaatgcag accggtgcca ccgatttact aatggtacct      420
ataaaaaatt attattttt aaaaaattga tgtgaccagt ggttggagag agaggtctac        480
cgattggtca agtggcacca attttttatt ttacctcctg cctagattcg taaatactat      540
tgcatttatc tcatttcatt atttatttaa ttattttata ttatttggat aaaaattcta      600
atactttact tttttttaaa aagaatttat ttaattattt tatattattt agataaaaat      660
tctaatactt tacttttttt ttaaaaagaa tttcaattgc gttttttctt aatttagttt      720
taattctata ctaattataa aaattctgat cggattagtg tggtgtcaaa gtcaagtcac      780
atgaattttg ttggagaaaa aataaaaatt aaacacattt ttcgattaat ttattatata      840
tataataata taaacacatt tttatttaat gttgtcaata atattttta attaaaattt        900 cagcacaaca attacactct catcattaaa tttaatctta ttaccataat taaaattgtg      960
aggacaatta ttttttaatc tcaccctcca ttaatgcata ttattaattt ttgttcgata      1020
cttcttattt cactcctaac attaatcatt aacccaattt tgaactgtta taatttctta     1080
acttattcac tattgtggct ctgggtccat ctggaaaggc caccgtccag gctgtccaac     1140
cacactttgc cacgtcatca attccagtaa ctacattgtt acagttacta agcaaatccc     1200
aatttcaaaa attcaatttc ccaggaaaac gaaacgtccg ttactaaccg acctaaaacc     1260
cagctcaacc tgccgtcaat taacggaaat cttttaactc ctctatataa cccaaaacca     1320
ctctcatcac catttcccca taaaagaat tccggaatt cttattcctt ttatattttt       1380
cctctccaat ttcccgtcac tttccggaga aaatgagaga aatccttcac atc            1433
```

ISOLATION AND CHARACTERIZATION OF A FIBER-SPECIFIC β-TUBULIN PROMOTER FROM COTTON

TECHNICAL FIELD

The present invention relates to the field of plant molecular biology, in particular to transgenic plants and promoters useful in creating transgenic plants, and more particularly to fiber-specific promoters.

BACKGROUND OF THE INVENTION

Cotton is the most extensively used natural fiber in the textile industry. Annual production of cotton worldwide is over 100 million bales valued at 45 billion U.S. dollars. Although significant improvements have been made in quality and yield of the fibers by means of classical breeding in the past decades, the potential for further improving fiber properties through classical breeding is limited due to requirements for species compatibility and available traits. Genetic engineering provides novel approaches for further improving cotton by introducing genes to create new germplasms with highly desirable characteristics.

Cotton fibers (seed hairs) are single-cell trichomes that undergo rapid and synchronous elongation. Cortical microtubules provide spatial information necessary for the alignment of cellulose microfibrils that confine and regulate cell elongation [Giddings and Staehelin, 1991; Cyr and Palevitz, 1995; Fisher and Cyr, 1995]. Fiber development consists of four overlapping stages (i.e. initiation, primary cell wall formation, secondary cell wall formation and maturation) [Basra and Malik, 1984]. Tubulins and actins may play functionally important roles in developing fiber cells. Mature fiber is a biological composite of cellulose, water, small quantities of proteins, pectins, hemicellulose, mineral substances, wax, small amounts of organic acids, sugars, and pigments that provides excellent wearability and aesthetics [Arthur, 1990; Basra and Malik, 1984; Ryser, 1985]. Many genes are required for the fiber differentiation and development. These genes are differentially expressed during different stages of the fiber development, and so far only a few of the genes involved in the biosynthesis of the large numbers of fiber-specific structural proteins, enzymes, polysaccharides, waxes or lignins have been identified [John and Crow, 1992; John, 1996a; Song and Allen, 1997; Ma et al., 1997; Kawai et al., 1998; Whittaker and Triplett, 1999]. These isolated genes may be considered as having potential application in cotton fiber improvement due to the character of their fiber-specific expression. For example, John has been using fiber-specific gene promoters to produce genetically engineering cotton for altered fibers [John, 1996b, 1997a, 1997b].

A promoter is a DNA fragment that determines temporal and spatial specificity of gene expression during plant and animal development. Many tissue-specific genes and their promoters were identified and isolated from a wide variety of plants and animals over the past decade, including some cotton tissue-specific genes and promoters (Loguerico et al., 1999; Kawai et al., 1998; Song and Allen, 1997; Ma et al, 1997; John, 1996a; Rinehart et al., 1996; Hasenfratz et al, 1995; John and Peterson, 1994; John and Crow, 1992). A few promoters have been shown to control gene expression in a fiber-specific manner in cotton (Rinehart et al., 1996; John, 1996a; John and Crow, 1992). Some plant tissue-specific promoters can be utilized to express foreign proteins in specific tissues in a developmentally regulated pattern [John, 1996b, 1997a, 1997b].

SUMMARY OF THE INVENTION

A fiber-specific gene (named CFTUB2), encoding β-tubulin, was isolated from cotton. The isolated complete CFTUB2 cDNA is 1.623 kb in length including 1.338 kb of open reading frame. Based on the CFTUB2 cDNA sequence, two CFTUB2 promoter fragments (1.433 kb and 0.984 kb) were isolated from cotton. The two CFTUB2 promoter fragments (1.3 and 0.9 kb) were fused with the GUS gene to construct gene expression vectors for analyzing the function of the promoter. Transgenic cotton and tobacco plants with the CFTUB2 promoter/GUS fusion genes were identified by Southern blot hybridization. In all the transgenic cotton plants studied, GUS activity was detected only in young fibers, but not in the flower organs such as anthers, petals and sepals, or in leaves and roots. This result, together with Northern blot analysis, indicates that the CFTUB2 promoter is fiber-specific in cotton. The promoter controls specific gene expression at the transcriptional level in cotton fibers. The isolated promoter may be used in improving cotton fibers to create new cotton varieties with high fiber quality and yield by gene manipulation.

BRIEF DESCRIPTION OF THE FIGURES

FIG. 1 shows the nucleotide sequence of the cotton CFTUB2 gene cDNA (1623 bp; SEQ ID NO: 1).

FIG. 2 shows the nucleotide sequence of the isolated 1433 bp CFTUB2 promoter fragment (SEQ ID NO: 2. The 984 bp fragment corresponds to nucleotides 449–1433 of this sequence.

FIG. 3 shows constructs of the CFTUB2 promoter fused with the gus gene in expression vectors.

DETAILED DESCRIPTION

The CFTUB2 promoter is an active fiber-specific promoter in cotton. Results of a Northern blot analysis of cDNAs from a variety of cotton tissues showed that a cDNA clone comprising the CFTUB2 gene was strongly expressed in young fibers of 8 and 14 days postanthesis (DPA), and also expressed in young ovules of 4, 8 and 14 DPA, but less or not at all in other tissues. Sequencing of the cDNA clone revealed that it was 1623 bp in length containing a open reading frame of 1338 bp (FIG. 1). Comparing the nucleotide and predicted polypeptide sequences of the cotton CFTUB2 with the data banks, it was found that the CFTUB2 cDNA shared 96%–98% homology at the amino acid level and over 78% homology at the nucleotide level with the known β-tubulin cDNAs and genes from other plants (such as *Arabidopsis*, tobacco, rice, soybean, maize, potato, carrot, etc.) [Liaud et al., 1992; Snustad et al., 1992; Villemur et al, 1994; Tonoike, et al., 1994; Taylor et al., 1994; Kang et al., 1994; Okamura et al., 1997; Chu et al., 1998; Okamura et al., 1999].

The transcripts of the CFTUB2 gene exhibited the highest accumulation in cotton young fibers of 8 DPA, and then there was a visible decrease in the accumulation of the gene products (mRNA) with further development of the fibers. Comparison of gene expression in different developmental stages of cotton ovules also showed that the gene transcripts accumulated more in 8 DPA ovules than in 4 and 14 DPA, and there was a gradual and visible decrease to an undetectable level in the accumulation of gene products with fiber development from 8 DPA to 28 DPA. This suggests that the gene is specifically expressed with a strict regulation at the transcriptional level during cotton fiber and ovule development, as with other cotton fiber-specific genes [Whittaker and Triplett, 1999; Shin and Brown, 1999; Kawai et al., 1998; John, 1996a; Song and Allen, 1997; Ma et al, 1997; Rinehart et al., 1996; John and Crow, 1992].

Two fragments in the promoter region were isolated and cloned into pGEM-T vector, respectively. One fragment of the CFTUB2 promoter was 1433 bp in length (FIG. 2), and another was 984 bp long. Both fragments functioned as active, fiber-specific promoters. The constructs of CFTUB2 promoter/GUS fusion gene were used to transform tobacco and cotton by *Agrobacterium*-mediated gene transfer, using the pBI121 vector containing CaMV35S promoter/GUS fusion as a positive control. Consistent with the results from Northern blot analysis, the GUS gene driven by CFTUB2 promoter specifically expressed in the young fibers, but not in other tissues, in all the 31 transgenic cotton plants studied, while the GUS activity was detected in all the tissues of positive control cotton plants (35S:GUS). A total of 36 transformed cotton plants were obtained and transplanted in soil to grow to maturation. Similarly, it was found that under the CFTUB2 promoter, GUS gene activity was only detected in the seeds in all of the 15 transgenic tobacco plants studied, suggesting the CFTUB2 promoter activity was also tissue-specific in tobacco (the cotton fiber, being an elongated hair of the seed coat, finds histological correspondence in the tobacco seed coat). This result, together with the above Northern blot analysis, indicates that the CFTUB2 promoter controls gene specific expression at the transcriptional level in cotton fibers.

Accordingly, one embodiment of the present invention is a fiber-specific promoter obtained from the cotton fiber β-tubulin gene CFTUB2.

Another embodiment of the present invention is a fiber-specific promoter comprising a 1433 kb active fragment of the cotton fiber CFTUB2 gene promoter.

Another embodiment of the present invention is a fiber-specific promoter comprising a 984 kb active fragment of the cotton fiber CFTUB2 gene promoter.

Stll another embodiment of the present invention is a promoter that is cotton fiber-specific comprising an active fragment of the CFTUB2 promoter fragment of SEQ ID NO: 2. An active fragment is a sequence of shorter length than SEQ ID NO: 2 which still retains activity as a fiber-specific promoter in cotton. A fragment can comprise excisions, deletions, truncations or substitutions of the sequence of SEQ ID NO: 2, or a combination of these. A preferred active fragment is the fragment consisting of nucleotides 449–1433 of SEQ ID NO: 2.

The promoters of the present invention are useful in creating transgenic cotton having altered fiber characteristics. The use of the fiber-specific promoters of the present invention permits selective expression of a transgene in the cotton fiber, permitting greater latitude in the types of transgenes employed. Selective expression avoids problems such as the metabolic burden imposed on a transgenic plant by systemic expression of a transgene, or the adverse effects of the expression of a transgene in non-fiber tissues. Examples for expressing desirable genes in cotton fiber, but not in other parts of the cotton plants include: (1) anthocynin genes for colored cotton, (2) silk protein genes from silk worm or spiders for increased strength of cotton fiber, (3) and biosynthesis of polyhydroxybutrate in cotton fiber for improved thermal properties and insulating characteristics [John, et al., 1996]. There are numerous examples in the art of fiber-enhancing genes that could be advantageously linked to the promoters of the present invention, and used to transform cotton using well-known techniques (see, e.g., Umbeck, 1992), to achieve expression of the transgene in transgenic cotton fibers. See e.g., John, 1996b, 1997a, 1997b; John et al., 1996.

EXAMPLE 1

Isolation of Fiber-Specific cDNA Encoding CFTUB2 Sequences Expressed Early During Fiber Development of Cotton Cotton seeds were surface-sterilized with 70% ethanol for 30–60 seconds and 10% $H_2O_2$ for 30–60 minutes, followed by washing with sterile water. The seeds germinated on ½ MS medium on light at 28° C. in a culture room, and cotyledons and hypocotyls cut from sterile seedlings were used as transformation explant materials. Cotton plants were grown in pots for DNA and RNA extraction.

Total RNA was extracted from young fibers, ovaries, anthers, petals, sepals, leaves and roots of cotton by using the guanidinium thiocyanate method or SV Total RNA Isolation System (Promega). Poly(A)+ RNA was purified by using oligo(dT)-cellulose spin columns from an mRNA purification kit (Pharmacia Biotech). Cotton cDNA was synthesized by using a cDNA synthesis kit (Pharmacia Biotech). Cotton cDNA libraries were constructed by inserting the cDNA fragments into the ZAP express vector (Stratagene).

Poly(A)+ RNAs from cotton young fibers of about 8 and 14 days postanthesis (DPA), respectively, were converted to cDNAs which were used to construct cotton cDNA libraries. From the fiber cDNA libraries, about 200 cDNA clones were randomly picked out and subsequently sequenced. Some clones with potential involvement in cell expansion were selected according to the sequence data.

To find cDNA clones whose transcripts are specifically expressed in cotton fibers, the expression pattern of the selected cDNA clones was analyzed by Northern blot hybridization with total RNAs isolated from cotton fibers, ovules, anthers, petals, sepals, squares, leaves and roots, using probes from the clones. RNA samples from the different cotton tissues were separated on agarose-formaldehyde gels, and transferred onto Hybond-N nylon membranes by capillary blotting. RNA Northern blots were hybridized in ExpressHyb solution (Clontech) at 68° C. with $^{32}P$ cDNA probes prepared by random labeling (Promega Prime-a-Gene Labeling System). After hybridization, the blots were washed at 68° C. in 0.1×SSC, 0.5% SDS for 30–60 minutes. The experimental results showed that one cDNA clone strongly expressed in young fibers of 8 and 14 DPA, and also expressed in young ovules of 4, 8 and 14 DPA, but less or not at all in other tissues.

PCR fragments and cDNA fragments were subcloned into vectors, and plasmid DNA prepared with a Qiagen plasmid kit was used as templates in PCR reactions. The PCR products were sequenced by autosequencer. Sequencing of the cDNA clone revealed that it was 1623 bp in length containing a open reading frame of 1338 bp, and identical to the β-tubulin gene (FIG. 1). This is the first CFTUB2 cDNA clone isolated from cotton. Comparing the nucleotide and predicted polypeptide sequences of the cotton CFTUB2 with the data banks, it was found that the CFTUB2 cDNA shared 96%–98% homology at the amino acid level and over 78% homology at the nucleotide level with the known β-tubulin cDNAs and genes from other plants (such as *Arabidopsis*, tobacco, rice, soybean, maize, potato, carrot, etc.) [Liaud et al., 1992; Snustad et al., 1992; Villemur et al, 1994; Tonoike, et al., 1994; Taylor et al., 1994; Kang et al., 1994; Okamura et al., 1997; Chu et al., 1998; Okamura et al., 1999].

Total RNAs from different tissues of cotton were used to reverse-transcribe first-strand cDNAs which were used as templates in differential display PCR reactions. Differential display analysis was carried out by using a differential display kit (Clontech). First-strand cDNA was synthesized with 2 pg total RNA as starting materials of reverse transcription and oligo(dT) as primers at 42° C. for 1 hour. Differential display PCR reactions were carried out with a initial cycle consisting of 94° C. for 5 minutes, 40° C. for 5 minutes and 68° C. for 5 minutes, followed by two cycles consisting of 94° C. for 2 minutes and 40° C. for 5 minutes and 68° C. for 5 minutes, and then 25 cycles consisting of 94° C. for 1 minute and 60° C. for 1 minute and 68° C. for 2 minutes, and a final extension at 68° C. for 7 minutes. Target differential display bands were excised and reamplified for further analysis. Reproducible fiber-specific differential display products were targeted for further analysis. The cDNA in each target band was harvested and regenerated by PCR amplification. The isolated cDNA was subsequently subcloned into vectors and sequenced.

The Northern blot analysis showed that the transcripts of the CFTUB2 gene exhibited a highest accumulation in cotton young fibers of 8 DPA, and then there was a visible decrease in the accumulation of the gene products (mRNA) with further development of the fibers. Comparison of gene expression in different developmental stages of cotton ovules also showed that the gene transcripts accumulated more in 8 DPA ovules than in 4 and 14 DPA, and there was a gradual and visible decrease to an undetectable level in the accumulation of gene products with fiber development from 8 DPA to 28 DPA. This suggests that the gene is specifically expressed with a strict regulation at the transcriptional level during cotton fiber and ovule development, as seen with other cotton fiber-specific genes [Whittaker and Triplett, 1999; Shin and Brown, 1999; Kawai et al., 1998; John, 1996a; Song and Allen, 1997; Ma et al, 1997; Rinehart et al., 1996; John and Crow, 1992].

EXAMPLE 2

Isolation of the CFTUB2 Promoter

Based on the screened CFTUB2 cDNA sequence, the CFTUB2 promoter was isolated from cotton Genome Walker libraries by Genome Walker PCR.

Total DNA was extracted and purified from leaves of cotton plants by using the following method. Liquid $N_2$ was added to 4 g of leaf tissues, and the leaves were homogenized thoroughly. 20 ml ice-cold extraction buffer (63 g/L glucose, 0.1 M Tris.HCl (pH 8.0), 5 mM EDTA, 20 g/L PVP-40, 1 g/L DIECA, 1 g/L ascorbic acid, 2 ml/L, betamercaptoethanol) was added to the homogenized tissues in a 50 ml tube and centrifuged at 2500 rpm for 15 minutes. After removing the supernatant, 10 ml lysis buffer was added to each tube. The resuspended pellets were incubated at 65° C. for 30 minutes. 10 ml chloroform was added to each tube, mixed with the samples and centrifuged at 3500 rpm for 10 minutes. The supernatant was transferred to a clean tube, and chloroform extraction was repeated one more time. The supernatant was transferred to a clean tube, and 0.6 volume isopropanol was added to each tube for DNA precipitation. After centrifuging at 3500 rpm for 30 minutes, the DNA was washed with 70% ethanol. The isolated genomic DNA was then dissolved in sterile water or TE (10 mM Tris.HCl, 1 mM EDTA) for use.

Cotton genomic DNA libraries were constructed from leaves of cotton plants. DNA was partially digested with BamH I, and the DNA fragments were cloned in the BamH I site of the ZAP expression vector (Stratagene).

Genome Walker libraries were constructed by using Universal Genome Walker kit (Clontech). Genomic DNA from leaves of cotton plants was digested with five restriction enzymes respectively, and then purified by phenol/chloroform and precipitated by ethanol. Digested DNA was ligated to Genome Walker adaptors. Two rounds of Genome Walker PCR reactions were carried out successively. 1 µl of each Genome Walker DNA library was used as templates in the primary PCR, and the primary PCR products were used as templates in secondary PCR. The PCR was started at 95° C. for 1 minute, followed by 35 cycles consisting of 95° C. for 15 seconds and 68° C. for 4 minutes, and a final extension at 68° C. for 6 minutes. Target PCR bands were cut out and purified by Geneclean kit (Bio 101).

Two fragments in the promoter region were isolated and cloned into pGEM-T vector, respectively. One fragment of the CFTUB2 promoter was 1433 bp in length FIG. 2, and another was 984 bp long. FIG. 2. A Hind III site and a BamH I site were created at the 5'-end and 3'-end of the 0.9 kb CFTUB2 promoter fragment of cotton respectively by PCR method. The Hind III/BamH I fragment was initially subcloned into pGEM-T vector (Promega). Plasmid DNA containing the CFTUB2 promoter fragment was digested with Hind III and BamH I, and the digested fragment was isolated by agarose gel electrophoresis. A chimeric CFTUB2 promoter/GUS construct was generated by insertion of the fragment, replacing CaMV 35S promoter, into the Hind III/BamH I sites of pBI121 vector.

The 1.3 kb of BamH I/BamH I CFTUB2 promoter fragment was initially subcloned into the pGEM-T vector (Promega). Plasmid DNA containing the CFTUB2 promoter fragment was digested with BamH I, and the digested fragment was isolated by agarose gel electrophoresis. A chimeric CFTUB2 promoter/GUS construct was generated by insertion of the fragment into the BamH I site of pBI101 vector.

EXAMPLE 3

Functional Analysis of the CFTUB2 Promoter

In order to characterize the function of CFTUB2 promoter in fiber-specific expression of the CFTUB2 gene, a 1.3 kb of fragment and a 0.9 kb of fragment of the CFTUB2 promoter were fused with gus coding sequence in the gene expression vector pBI101 or pBI121 (deleting CaMV35S promoter), respectively (FIG. 3). The constructs of CFTUB2 promoter/GUS fusion gene were used to transform tobacco and cotton by *Agrobacterium*-mediated gene transfer, using the pBI121 vector containing CaMV35S promoter/GUS fusion as a positive control. The CaMV35S promoter is active in all the tissues of cotton and other plants and is a constitutive promoter [Odell et al., 1985; Ow et al., 1987; McCabe and Martinell, 1993]. A binary vector containing either a CFTUB2 promoter/GUS fusion gene or the CaMV35S promoter/GUS control control was transferred into *Agrobacterium tumefaciens* strain LBA 4404. Cotton explants for transformation were obtained from cotton seedlings grown as in Example 1. Tobacco explant material was obtained from tobacco seedlings. Tobacco seeds were surface-sterilized with 70% ethanol for 30–60 seconds and 0.1% $HgCl_2$ for 15 minutes, followed by washing with sterile water. The seeds germinated on ½ MS medium on light at 28° C. in culture room, and leaves cut from sterile seedlings for use as explants for transformation. Cotton cotyledon and hypocotyl explants and tobacco leaf explants were transformed by the *Agrobacterium* with the vectors, and transformed plants were transplanted to soil in greenhouse for growing to maturity.

Tobacco leaves were cut into about 2×2 cm pieces, and immersed in *Agrobacterium* suspension for 5 minutes. The infected tobacco explants were cultivated on MS medium with 1 mg/L 6-BA for 48 hours at 28° C., and then transferred onto selection MS medium containing 100 mg/L kanamycin and 1 mg/L 6 -BA for 20–30 days for selecting transformed shoots (kanamycin-resistant shoots). The transformed shoots were cut from the calli and rooted on MS medium with 50–100 mg/L kanamycin. The transformed tobacco plants were transplanted to soil in greenhouse for growing to maturity.

The cotyledon and hypocotyl were used as explants for cotton transformation. Cotton seeds were surface-sterilized with 70% ethanol for 30 seconds and 10% $H_2O_2$ for 60 minutes, followed by washing with steril water. These seeds were incubated in the sterile water at 28° C. After over night, the seeds sprouted. The embryos were taken out and put on the IM medium (½ {MS (macronutriants, micronutrients, EDTA-Fe)+VB1 10 mg/L+VB6 1 mg/L+VPP 1 mg/L+Myo-Insitol 100 mg/L}+phytogel 2 g/L pH=6.4) at 28° C. for 7 days. The cotyledon and hypocotyl of cotton were used as explants for transformation. After cutting into 5 $mm^2$ (mm) piece, the explants were soaked in the *Agrobacterium tumefaciens* strain LBA 4404 suspension ($OD_{600}$=0.2–0.4) for 15 minutes. Then the explants were put on CM medium (MS (macronutriants, micronutrients, EDTA-Fe)+VB1 10 mg/L+VB6 1 mg/L+VPP 1 mg/L+Myo-Instiol 100 mg/L+2.4-D 0.1 mg/L+KT 0.1 mg/L+Glucose 30 g/L+$MgCl_2$ 0.7 mg/L+phytogel 2 g/L pH=6.4) at 24° C. for 2 days. After washing with liquid MS medium, the explants were put on the SM medium (MS (macronutriants, micronutrients, EDTA-Fe)+VB1 10 mg/L+VB6 1 mg/L=VPP 1 mg/L+Myo-Insitol 100 mg/L+2.4-D 0.1 mg/L+KT 0.1 mg/L+Glucose 30 g/L+$MgCl_2$ 0.7 mg/L+phytogel 2 g/L+Kanamycin 50 mg/L+Cefutoxime 200 mg/L pH=6.4) on light at 28° C. in culture room for selecting and the subculture was per month. After 2–3 months subculturing on SM, the calli were induced from explants. The calli were transferred on DM medium (MS (macronutriants, micronutrients, EDTA-Fe)+VB1 10 mg/L+VB6 1 mg/L+VPP 1 mg/L+Myo-Insitol 100 mg/L+$KNO_3$ 19 g/L+$MgCl_2$ 0.7 mg/L+Glucose 30 g/L+phytogel 3 g/L pH=6.4) and subcultured per month. After about 5 months, the somatic embryos begin to form. Continuing to culture the young embryos on DM medium until they develop into maturity. The mature embryos were transferred on GM medium (½ {MS (macronutriants, micronutrients, EDTA-Fe)+VB1 10 mg/L+VB6 1 mg/L+VPP 1 mg/L+Myo-Insitol 100 mg/L)+NAA 0.01 mg/L+Glucose 30 g/L+phytogel 3.5 g/L pH=6.4) in the box for developing into plantlets. And then the plantlets were transplanted in the soil for the plant growing and collecting the transgenic seeds.

Transgenic tobacco and cotton plants possessing the chimeric CFTUB2 promoter/GUS gene (or $^{35}$S:GUS gene), and non-transformed plants as negative controls, were analyzed by DNA Southern blot hybridization and by GUS histochemical assay. Total genomic DNA from cotton and tobacco leaves were digested with restriction enzymes, separated on agarose gels, and transferred onto Hybond-N nylon membranes by capillary blotting. DNA Southern blots were hybridized in ExpressHyb solution (Clontech) at 68° C. with $^{32}$P-DNA probes prepared by random labeling (Promega Prime-a-Gene Labeling System). After hybridization, the blots were washed at 68° C. in 0.1×SSC, 0.5% SDS for 30–60 minutes. The $^{32}$P-labeled nylon membranes were exposed to X-ray film at −70° C. for autoradiography. The results of Southern blot analysis demonstrated that CFTUB2 promoter/GUS gene was integrated into tobacco and cotton genomes. Total of 325 transformed cotton plants, which belong to 31 transformed lines, were obtained and transplanted in soil to grow to maturation.

Histochemical assays for GUS activity in transgenic tobacco and cotton plants were conducted according to the protocol described previously by Jefferson et al. (1987) with some modifications. Fresh tissues from the plants were incubated in X-gluc (5-bromo-4-chloro-3-indolylglucuronide) solution consisting of 0.1 M sodium phosphate (pH 7.0), 10 mM ethylene diaminetetraacetic acid (EDTA), 0.5 mM potassium ferrocyanide and 0.5 mM potassium ferricyanide, and 0.1% X-gluc (Clontech chemical) overnight. The stained plant materials were then cleared and fixed by rinsing with 100% and 70% ethanol successively, and the samples were examined and photographed directly or under a microscope. Consistent with the results from Northern blot analysis, the GUS gene driven by CFTUB2 promoter specifically expressed in the young fibers, but not in other tissues, in all the 31 transgenic cotton plants studied, while the GUS activity was detected in all the tissues of positive control cotton plants ($^{35}$S:GUS). A total of 36 transformed cotton plants were obtained and transplanted in soil to grow to maturity, all of which had detectable GUS activity only in the young fibers, not in the flower organs such as anthers, petals and sepals, or in leaves and roots. Similarly, it was found that under the CFTUB2 promoter, GUS gene activity was only detected in the seeds in all of the 15 transgenic tobacco plants studied, suggesting the CFTUB2 promoter activity was also tissue-specific in tobacco. This result, together with the above Northern blot analysis, indicates that the CFTUB2 promoter controls gene specific expression at the transcriptional level in cotton fibers.

REFERENCES

An Y Q, Huang S, McDowell J M, 1996. Conserved expression of the *Arabidopsis* ACT1 and ACT3 actin subclass in organ primordia and mature pollen. Plant Cell, 8(1):15–30.

Arthur J C, 1990. In Polymers: Fibers and Textile, A Compendium, ed. Kroschwitz, J I. (Wiley, New York), pp. 118–141.

Baird W V and Meagher R B, 1987. A complex gene superfamily encodes actin in petunia. EMBO J., 6(11): 3223–31.

Basra A S and Malik C P, 1984. Development of the cotton fiber. Int. Rev. Cytol. 89:65–113.

Chu B, Wilson T J, McCune-Zierath C, Snustad D P, Carter J V., 1998. Two beta-tubulin genes, TUB1 and TUB8, of *Arabidopsis* exhibit largely nonoverlapping patterns of expression. Plant Mol. Biol., 37(5):785–90.

Cox G M, Rude T H, Dykstra C C, 1995. The actin gene from *Cryptococcus neoformans*: structure and phylogenetic analysis. J. Med. Vet. Mycol., 33(4):261–6.

Cyr R J and Palevitz B A, 1995. Organization of cortical microtubules in plant cells. Curr. Opin. Cell Biol., 7:65–71.

Fisher D D and Cyr R J, 1998. Extending the microtubule/microfibril paradigm. Plant Physiol., 116:1043–51.

Giddings T H and Staehelin L A, 1991. Microtubule-mediated control of microfibril deposition: a re-examination of the hypothesis. In C W Lloyd, ed., The Cytoskeletal Basis of Plant Growth and Form. Academic Press, London, pp. 85–99.

Hasenfratz M P, Tsou C L, Wilkins T A, 1995. Expression of two related vacuolar H(+)-ATPase 16-kilodalton proteolipid genes is differentially regulated in a tissue-specific manner. Plant Physiol., 108(4): 1395–404.

Jefferson R A, 1987. Assaying chimeric genes in plants: the GUS gene fusion system. Plant Mol. Biol. Rep., 5:387–405.

Jefferson R A, Kavanagh T A, Bevan M W, 1987. GUS fusion: p-glucuronidase as a sensitive and versatile gene fusion marker in higher plants. EMBO J., 6:3901

John M E and Crow L J, 1992. Gene expression in cotton fiber: cloning of the mRNAs. Proc. Natl. Acad. Sci. USA, 89(13):5769–73.

John M E and Peterson M W, 1994. Cotton pollen-specific polygalacturonase mRNA: tissue and temporal specificity of its promoter in transgenic tobacco. Plant Mol. Biol., 26(6):1989–93.

John M E, 1996a. Structural characterization of genes corresponding to cotton fiber mRNA, E6: reduced E6 protein in transgenic plants by antisense gene. Plant Mol. Biol., 30(2):297–306.

John, M E, 1996b. Genetically engineering cotton plants for altered fiber, U.S. Pat. No. 5,495,070.

John, M E, and Keller, G. 1996. Metabolic pathway engineering in cotton: Biosynthesis of polyhydroxybutratein fiber cells. Proc. Natl. Acad. Sci. USA. 93:12768–12773.

John, M E, 1997a. Transgenic cotton plants producing heterologous polyhydroxy(e) butyrate bioplastic, U.S. Pat. No. 5,602,321.

John, M E, 1997b. Genetically engineering cotton plants for altered fiber, U.S. Pat. No. 5,620,882 (1997).

Kang M S, Choi Y J, Kim M C, Lim C O, Hwang I, Cho M J., 1994. Isolation and characterization of two beta-tubulin cDNA clones from rice. Plant Mol. Biol., 26(6): 1975–9.

Kawai M, Aotsuka S, Uchimiya H, 1998. Isolation of a cotton CAP gene: a homologue of adenylyl cyclase-associated protein highly expressed during fiber elongation. Plant Cell Physiol., 39(12):1380–3.

Liaud M F, Brinkmann H, Cerff R., 1992. The beta-tubulin gene family of pea: primary structures, genomic organization and intron-dependent evolution of genes. Plant Mol. Biol., 18(4):639–51.

Loguerico L L, Zhang J Q, Wilkins T A, 1999. Differential regulation of six novel MYB-domain genes def two distinct expression patterns in allotetraploid cotton. Mol. Gen. Genet., 261(4/5):660–71.

Ma D P, Liu H C, Tan H, Creech R G, Jenkins J N, Chang Y F, 1997. Cloning and characterization of a cotton lipid transfer protein gene specifically expressed in fiber cells. Biochim. Biophys. Acta, 1344(2): 111–4.

McCabe D E and Martinell B J, 1993. Transformation of elite cotton cultivars via particle bombardment of meristems. Biotechnology, 11:596–8.

McElroy D, Rothenberg M, Reece K S, Wu R, 1990. Characterization of the rice actin gene family. Plant Mol. Biol., 15(2):257–68.

Nairn C J, Winesett L, Ferl R J, 1988. Nucleotide sequence of an actin gene from *Arabidopsis thaliana*. Gene, 65(2): 247–57.

Odell J T, Nagy F, Chua N-H, 1985. Identification of DNA sequences required for activity of the cauliflower mosaic virus 35S promoter. Nature, 313:810–2.

Okamura S, Naito K, Sonehara S, Ohkawa H, Kuramori S, Tatsuta M, Minamizono M, Kataoka T., 1997. Characterization of the carrot beta-tubulin gene coding a divergent isotype, beta-2. Cell Struct. Funct., 22(2):291–8.

Okamura S, Okahara K, Iida T, Ozaki M, Asano S, Morita M, Imanaka T, 1999. Isotype-specific changes in the amount of beta-tubulin RNA in synchronized tobacco BY2 cells. Cell Struct. Funct., 24(3): 117–22.

Ow D W, Jacobs J D, Howell S H, 1987. Functional regions of the cauliflower mosaic virus 35S RNA promoter determined by use of the firefly luciferase gene as a reporter of promoter activity. Proc. Natl. Acad. Sci. USA, 84:4870–4.

Rinehart J A, Peterson M W, John M E, 1996. Tissue-specific and developmental regulation of cotton gene FbL2A. Demonstration of promoter activity in transgenic plants. Plant Physiol., 112(3):1331–41.

Ryser U, 1985. Cell wall biosynthesis in differentiating cotton fibers. Eur. J. Cell Biol., 39:236–56.

Shah D M, Highrower R C, Meagher R B, 1983. Genes encoding actin in higher plants: intron positions are highly conserved but the coding sequences are not. J. Mol. Appl. Genet., 2(1): 111–26.

Shin H and Brown R M jr, 1999. GTPase activity and biochemical characterization of a recombinant cotton fiber annexin. Plant Physiol., 119(3):925–34.

Song P and Allen R D, 1997. Identification of a cotton fiber-specific acyl carrier protein cDNA by differential display. Biochim. Biophys. Acta, 1351(1):305–12.

Snustad D P, Haas N A, Kopczak S D, Silflow C D., 1992. The small genome of *Arabidopsis* contains at least nine expressed beta-tubulin genes. Plant Cell, 4(5):549–56.

Stranathan M, Hastings C, Trinh H, 1989. Molecular evolution of two actin genes from carrot. Plant Mol. Biol., 13(4):375–83.

Taylor M A, Wright F, Davies H V., 1994. Characterization of the cDNA clones of two beta-tubulin genes and their expression in the potato plant (*Solanum tuberosum* L.). Plant Mol. Biol., 26(3):1013–18.

Tonoike H, Han I S, Jongewaard I, Doyle M, Guiltinan M, Fosket D E, 1994. Hypocotyl expression and light down-regulation of the soybean tubulin gene, tubB1. Plant J., 5(3):343–51.

Umbeck, Paul, 1992. Genetic engineering of cotton plants and lines, U.S. Pat. No. 5,159,135.

Villemur R, Haas N A, Joyce C M, Snustad D P, Silflow C D, 1994. Characterization of four new beta-tubulin genes and their expression during male flower development in maize (*Zea mays* L.). Plant Mol. Biol., 24(2):295–315.

Whittaker D J and Triplett B A, 1999. Gene-specific changes in alpha-tubulin transcript accumulation in developing cotton fibers. Plant Physiol., 121(1):181–8.

We claim:

1. An isolated cotton fiber promoter comprising the promoter of the cotton β-tubulin gene CFTUB2 consisting of the sequence of SEQ ID NO:2.

2. An isolated cotton fiber promoter comprising the promoter of the cotton β-tubulin gene CFTUB2 consisting of the sequence of nucleotides 449–1433 of SEQ ID NO:2.

* * * * *